United States Patent [19]

Sessions et al.

[11] 4,069,826
[45] Jan. 24, 1978

[54] SURGICAL TUBE ADAPTER CLAMP

[75] Inventors: Robert William Sessions, Hinsdale; Jerome Jeslis, Chicago, both of Ill.

[73] Assignee: Barlow Mfg. Corporation, Hinsdale, Ill.

[21] Appl. No.: 720,252

[22] Filed: Sept. 3, 1976

[51] Int. Cl.² .................... A61M 25/00; A61M 5/00
[52] U.S. Cl. .................... 128/348; 128/214 R; 128/243
[58] Field of Search ......... 128/214 R, 214.4, 242–244, 128/245, 343, 345, 348–351

[56] References Cited

U.S. PATENT DOCUMENTS

| 1,636,969 | 7/1927 | Rose | 128/244 |
|---|---|---|---|
| 2,457,244 | 12/1948 | Lamson | 128/246 |
| 2,616,429 | 11/1952 | Merenlender | 128/350 R |
| 2,790,442 | 4/1957 | Donaldson | 128/348 |
| 3,108,595 | 10/1963 | Overment | 128/350 R |
| 3,154,079 | 10/1964 | McKay | 128/348 |
| 3,946,741 | 3/1976 | Adair | 128/349 R |

Primary Examiner—Dalton L. Truluck
Attorney, Agent, or Firm—Hill, Gross, Simpson, Van Santen, Steadman, Chiara & Simpson

[57] ABSTRACT

A surgical tube-adapter clamp for effecting a tube connection to a blood vessel, in which a tubular member is constructed for insertion of its free end into a blood vessel and the opposite end adapted to be operatively connected to the cooperable end of a tube, in which a pair of relatively deformable members, encircle the tubular member with one of such members being adapted to be disposed adjacent the exterior wall of the blood vessel and the other member having a portion disposed within the blood vessel and adapted to be deformed to increase the effective diameter thereof within the blood vessel and thereby clamp the adjacent wall of such vessel between the two deformable members to secure the clamp to the vessel.

7 Claims, 5 Drawing Figures

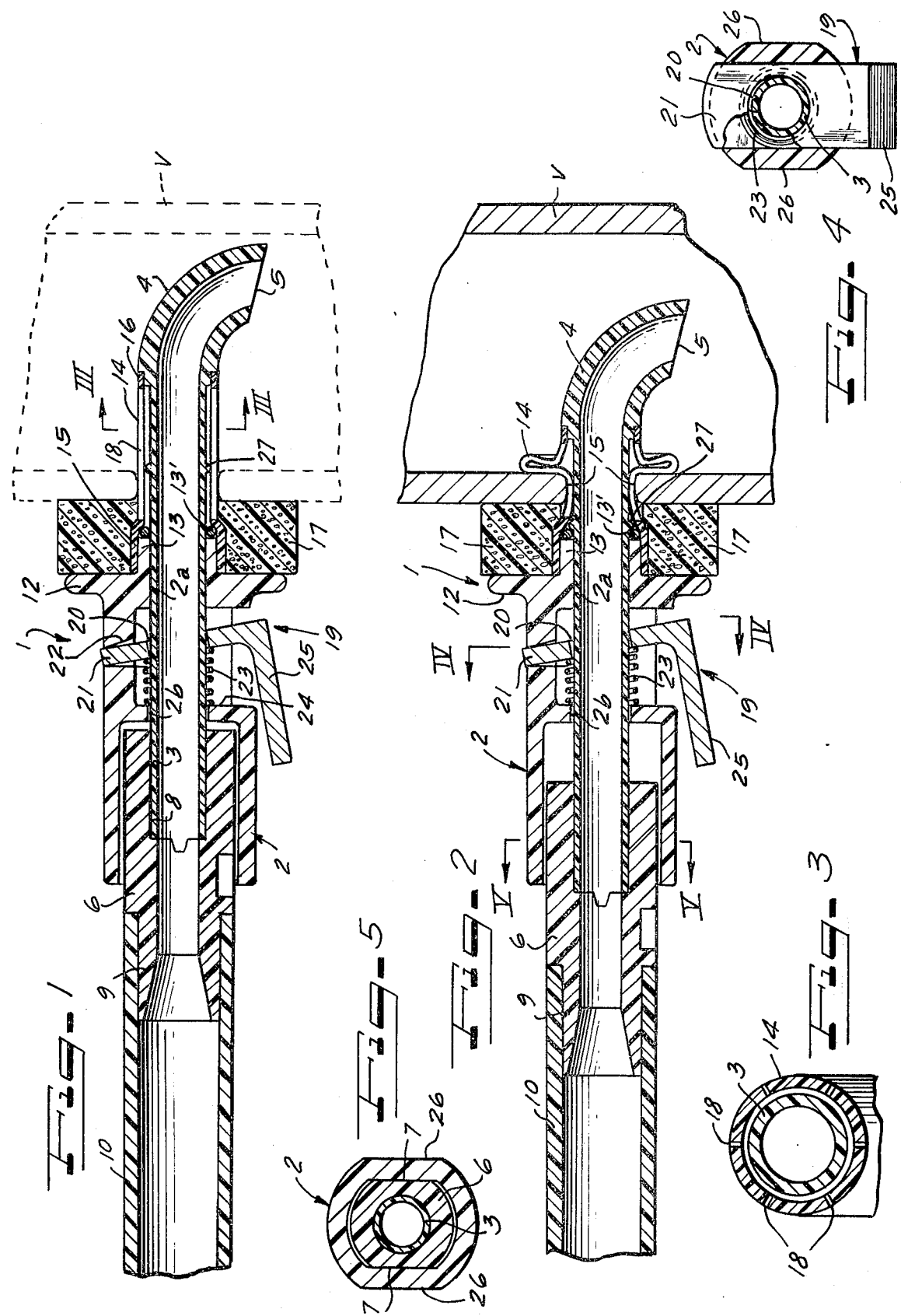

SURGICAL TUBE ADAPTER CLAMP

BACKGROUND OF THE INVENTION

The invention is directed to a surgical tube-adapter structure by means of which a fluid conducting tube may be operatively connected to a blood vessel for withdrawing blood from or inserting blood into the vessel.

Devices of this general type are employed in connection with surgical operations, particularly those involving open heart surgery and the like, wherein a by-pass structure may be formed for the flow of blood, to relieve blood pressure at the heart or particular point of surgery. Thus, loss of blood and hemorrhaging due to the otherwise increased blood pressure, which may reach 200 mm of mercury, is eliminated.

In the past, tube connections of this general type have been made by inserting the end of a tubular structure within the blood vessel and suturing such structure in position on the blood vessel. Devices of this construction have been prone to leakage and at the same time present a number of disadvantages in connection with their installation and removal. The physical operation attendant to the insertion of such tube and the suturing thereof to the blood vessel is both a time consuming and a very delicate operation as the suture should not extend completely through the wall of the blood vessel as this would create an additional leakage problem. Consequently, the surgeon endeavors to stitch merely into the wall without actually piercing it. It will be appreciated that such an operation cannot be hurriedly effected. Following the utilization of the connecting structure, the sutures must be cut and removed from the vessel along with the tubular structure, and the puncture in the vessel repaired. This is normally accomplished by means of a spoon clamp which has a generally spoon configuration and is provided with an opening in the spoon portion thereof to provide access to the puncture in the vessel whereby the puncture may be sutured, working through the hole in the clamp. Needless to say, such suturing and the attendant removal operations create trauma to the vessel.

BRIEF SUMMARY OF THE INVENTION

The present invention is directed to a tube-connecting structure which eliminates these disadvantages and which may be readily inserted and firmly clamped in position with the danger of leakage being reduced to substantially the absolute minimum, and with a minimum creation of trauma to the vessel.

The desired results are achieved in the present invention by constructing the device in the form of a clamping structure whereby the wall of the vessel is, in effect, clamped to the tube member inserted into the vessel, with means being provided for applying clamping pressures to the adjacent vessel sidewall both at the external and at the internal sides thereof. More particularly, the construction is such that the tubular insertion portion of the device carries two relatively deformable members, one of which is adapted to engage the outer wall surface of the vessel surrounding the inserted tubular member while the second member, within the vessel, is constructed to permit ready insertion thereof into the vessel, i.e. while the deformable member is in a relatively retracted state and thus has an effective diameter approximately corresponding to that of the inserted tubular member whereby it may be readily inserted therewith into the vessel.

However, when insertion has been fully made, expansion of the second deformable member within the vessel is suitably effected to increase the effective diameter of the deformable member, whereby the same will bear upon the inner wall surface of the vessel surrounding the inserted tube and, cooperating with the first deformable member, clamp the adjacent portion of the vessel wall between the two deformable members, thereby firmly mounting the device on the vessel, as well as effectively sealing the same thereat, and substantially completely eliminating the danger of leaking.

In the particular embodiment of the invention illustrated, the expansion of the inner deformable member is effected by relative axial movement of the inserted tubular member with respect to the external deformable member bearing on the outer surface of the vessel, thereby causing the inner deformable member to buckle upon itself forming an annular enlargement adapted to bear on the innerwall surface of the vessel.

The improved connector thus eliminates all suturing operations, permitting the structure to be quickly and efficiently mounted on the vessel wall, while at the same time providing a very effective fluid seal therebetween. It will be appreciated that as the pressure within the vessel may be 200 mm of mercury or higher, as previously mentioned, it is extremely important to provide an efficient seal. Further, as the invention enables the clamping action to take place within the vessel as well as without the vessel, a very durable connection is made, as compared with a mere suturing into the vessel tissue without passing through the vessel wall.

Further, as the only damage to the blood vessel is the puncturing thereof to receive the tubular structure, trauma to the vessel is materially reduced as compared with a sutured structure.

BRIEF DESCRIPTION OF THE DRAWINGS

In the drawings wherein like reference characters indicate like or corresponding parts:

FIG. 1 is a longitudinal section through a clamp structure, embodying the invention, with the parts thereof illustrated in their normal positions for insertion of the device into the blood vessel;

FIG. 2 is a longitudinal section corresponding to that of FIG. 1, illustrating the clamping positions of the respective parts following insertion;

FIG. 3 is a transverse sectional view taken approximately on the line III—III of FIG. 1;

FIG. 4 is a transverse sectional view taken approximately on the line IV—IV of FIG. 2; and FIG. 5 is a transverse sectional view taken approximately on the line V—V of FIG. 2.

DETAILED DESCRIPTION OF A PREFERRED EMBODIMENT OF THE INVENTION

Referring to the drawings, the adapter clamp, indicated generally by the reference numeral 1, comprises a body member indicated generally by the reference numeral 2 in aligned bores 2a, 2b of which is reciprocably mounted an elongated tube 3 having an outer free curved end 4 which, for example, may be formed on an angle as indicated at 5 to facilitate insertion of such end of the tube through an opening in a blood vessel or the like. Rigidly connected to the other end of the tube 3, for example by means of a press fit is a tube adapter member 6 of generally cylindrical cross-section, provided with flat side walls 7, and having a bore 8 therein and provided at its free end with a stem 9 adapted to be inserted in the free end of a length of flexible tubing 10 to secure the clamp device thereto. The member 2 is provided with oppositely disposed flat side walls 26 (as illustrated in FIG. 5), and at its end, adjacent the free end 4 of the tube 3, with an outwardly directed annular flange 12 and a central tubular boss or projection 13. Encircling the adjacent portion of the tube 3 is an expandable sleeve 14 made of suitable material, such as vinyl and, having its adjacent end 15 encircling and frictionally engaging the outer side wall of the boss 13 to securely mount the sleeve on the boss. The opposite end 16 of the sleeve 14 is attached to the adjacent end portion 4 of the tube which, as illustrated in FIG. 1, has an external diameter greater than the diameter of the remainder of the tube inserted into the body member 2, with the sleeve generally extending concentric to the latter. Also, mounted on the body member 2 is a sponge pad 17, constructed of a suitable non-absorbing material, as for example polyurethane, with the pad abutting the flange 12 of the body member. As a further protection against blood leakage at the junction of the tube 3 with the member 2, an O-ring 13' may be provided adjacent the end of the boss 13.

As illustrated in FIGS. 1, 2 and 3, the sleeve 14 is provided with a plurality of longitudinally extending slots 18 therein which extend from adjacent the end of the boss 13 to adjacent the end portion 4 of the tube 3.

As the tube 3 is reciprocable in the body member 2, upon movement of the tube in a retracting direction into the body member 2, i.e. to the left as viewed in FIGS. 1 and 2, the sleeve 14 may buckle, for example as illustrated in FIG. 2. Means are provided for retaining the tube in a retracted position, i.e. preventing extending movement of the tube, in the form of a latching structure comprising an L-shaped release lever 19 having an opening 20 therein of size to readily receive the adjacent portion of the tube 3 as illustrated in FIGS. 1, 2 and 4. The upper end 21 of the lever 19 is disposed in a slot 22 in the body member 2, whereby the member 19 may pivot slightly about its engagement with the member 2 to provide a cocking action of the release level relative to the tube. The release member is adapted to be urged into such a cocking position, i.e. tube restraining position, by a compression spring 23 which encircles the tube and bears at one end upon the adjacent portion of the member 16 and at its opposite end upon a wall or abutment 24 formed on the body member, which abutment contains the bore 2b. The opposite end 25 of the release member 19 forms a manually engageable handle which may be readily engaged by the thumb or four fingers of the surgeon whereby, upon the application of pressure to the handle portion 25, the lever is rocked in a clockwise direction as viewed in FIG. 1 to release the tube and permit movement thereof relative to the body member.

As illustrated in FIGS. 4, and 5, the generally tubular portion of the body 2 also may be provided with flat side walls 26 to facilitate handling of the structure and with the complemental flat walls 7 of the member 6, orients the member 6 relative to the member 2 and thus orientation of the curved end 4 of the tube 3.

In use, the surgeon will initially make an opening in the blood vessel to which the device is to be applied, with such opening being slightly smaller than the free end portion 4 of the tube and, by means of the particular shape of such free end, it may be readily inserted in the opening, tending to expand the same slightly as it is inserted. Such a vessel V is illustrated in dotted lines in FIG. 1, which illustrates the device fully inserted in the blood vessel whereby the outer surface thereof is disposed in engagement with the pad 17.

Following such full insertion, the outer free end of the adapter 6 and adjacent tubing 10 may be suitably gripped, and while retaining the body member 2 in position, the tube 3, may be retracted to a position approximating that illustrated in FIG. 2, the release member 19 readily permitting such retracting movement of the tube but preventing the tube from returning to its original position. Such retraction will result in a deforming, i.e., a buckling of the sleeve 14 whereby the various sections thereof between the slots 18 will assume a shape approximating that illustrated in FIG. 2, to thereby firmly engage the inner surface of the vessel side wall and cooperating with the pad 17 to apply clamping forces to an annular portion of the vessel V surrounding the tube and sleeve. The pad 17 forms a very efficient seal between the clamp structure and the vessel side wall, while the O-ring 13' effectively seals the joint between the tube 3 and member 2. To insure optimum deformation of the sleeve 14, means are provided for limiting the deformation movement thereof. In the embodiment illustrated such means is operative to restrict further inward movement of the tubular member 3 relative to the body member 4, when the parts are in the relative positions illustrated in FIG. 2. In this embodiment, such means is in the form of an annular flange or projection 27 integrally formed on the tube 3, which extends radially outward therefrom and is axially positioned to engage the O-ring 13, when the structure is in the desired position, thereby preventing further inward movement of the tube, and corresponding further deformation of the sleeve 14.

Obviously, the insertion operation can be effected in a very short time, particularly as compared with a suturing operation, and at the same time minimum trauma to the vessel results. When it is desired to remove the device, the handle 25 of the release lever 19 is actuated against the opposition of the spring 23 to permit the tube and sleeve to resume their original positions, at which time the device may be readily withdrawn from the blood vessel.

It will be appreciated that the structure is exceedingly simple and while it may be readily constructed from materials which may be sterilized to permit reuse of the structure, the device is sufficiently simple and inexpensive to enable it to be employed as a disposable unit which may be discarded after a single use.

Having thus described our invention, it will be obvious that although various minor modifications might be suggested by those versed in the art, it should be understood that we wish to embody within the scope of the patent granted hereon all such modifications as reasonably and properly come within the scope of our contribution to the art.

We claim as our invention:

1. A surgical tube adapter clamp for effecting a tube connection to a blood vessel, the combination of a relatively rigid hollow tubular member having a free end constructed for insertion in a blood vessel, the opposite end adapted to be operatively connected to the cooperable end of a tube, a first relatively deformable member encircling said tubular member at a point spaced from said free end thereof and adapted to engage the adjacent external wall surface of a blood vessel following insertion therein of said free end, a second relatively deformable member, in the form of a tubular sleeve adapted to be expanded in a radial direction by relative axial movement of its free end portions toward one another, which sleeve encircles an intermediate portion of said tubular member and extends axially outwardly from said first deformable manner, whereby the outer end portion of said second deformable member may also be disposed in such a blood vessel, a body member in which said tubular member is supported for longitudinal movement, one end of said tubular sleeve being engaged with said body member and the opposite end engaged with said tubular member, whereby longitudinal movement of said tubular member relative to said body member is operable to effect expanding movement of said sleeve, for effecting a deformation of said sleeve to increase the effective diameter thereof within the blood vessel and thereby clamp the adjacent wall of such a vessel between the two deformable members to secure the clamp to the vessel, and releasable means engageable with said body and tubular member for retaining said tubular member in sleeve-expanding position relative to said body member, said releasable means comprising a lever, pivotally movable relative to said body member, and having an opening therein through which said tubular member extends, and resilient means for urging said lever in a direction to retain said tubular member in such retaining position.

2. A surgical tube adapter clamp according to claim 1, wherein said first deformable member is a pad of non-absorbing material.

3. A surgical tube adapter clamp according to claim 1, wherein said body member is provided with an elongated bore in which is slidably carried an adapter member having an outer free end constructed for engagement with an end of the tube to be connected to such a blood vessel, and an inner end to which the inner end of said tubular member is connected.

4. A surgical tube adapter clamp according to claim 3, wherein said body member is provided with an outwardly extending annular flange having a face engaged with said pad and adapted to apply clamping pressure thereto.

5. A surgical tube adapter clamp according to claim 4, wherein said body member is provided with a cylindrical boss, extending outwardly from said flange, on which the adjacent end of said sleeve is mounted.

6. A surgical tube adapter clamp according to claim 5, wherein an O-ring is disposed adjacent the end of said boss and encircling said tubular member to provide a seal therebetween.

7. A surgical tube adapter clamp according to claim 10, wherein said tubular member is provided with an annular, outwardly extending projection disposed to engage said O-ring when said tubular member is in a position, relative to said body member, to provide desired deformation of said sleeve, and thereby restrict further inward movement of said tubular member.

* * * * *